(12) United States Patent  
Liu et al.

(10) Patent No.: US 10,827,984 B2
(45) Date of Patent: Nov. 10, 2020

(54) MONITORING DEVICE AND METHOD FOR PROVIDING GUIDANCE INFORMATION DURING A MEASUREMENT OPERATION

(71) Applicant: SHENZHEN MINDRAY BIO-MEDICAL ELECTRONICS CO., LTD., Shenzhen (CN)

(72) Inventors: Yang Liu, Shenzhen (CN); Qinglin Tao, Shenzhen (CN); Zhuomin Deng, Shenzhen (CN); Hexian Zhong, Shenzhen (CN); Weijun Wu, Shenzhen (CN); Jie Qin, Shenzhen (CN); Jianhui Zhang, Shenzhen (CN); Lei Qing, Shenzhen (CN); Mingyu Chen, Shenzhen (CN)

(73) Assignees: SHENZHEN MINDRAY BIO-MEDICAL ELECTRONICS CO., LTD, Shenzhen (CN); SHENZHEN MINDRAY SCIENTIFIC CO., LTD, Shenzhen (CN)

( * ) Notice: Subject to any disclaimer, the term of this patent is extended or adjusted under 35 U.S.C. 154(b) by 0 days.

(21) Appl. No.: 15/953,147

(22) Filed: Apr. 13, 2018

(65) Prior Publication Data
US 2018/0242922 A1    Aug. 30, 2018

Related U.S. Application Data

(63) Continuation of application No. PCT/CN2015/092133, filed on Oct. 16, 2015.

(51) Int. Cl.
*G06F 3/0481* (2013.01)
*A61B 5/00* (2006.01)
(Continued)

(52) U.S. Cl.
CPC .......... *A61B 5/743* (2013.01); *A61B 5/02055* (2013.01); *A61B 5/7435* (2013.01);
(Continued)

(58) Field of Classification Search
CPC ....... G06F 3/016; A61B 5/743; A61B 5/0002; A61B 5/02055; A61B 5/746; A61B 5/7275
See application file for complete search history.

(56) References Cited

U.S. PATENT DOCUMENTS

| 2006/0184052 A1* | 8/2006 | Iwasawa | A61B 5/022 600/485 |
| 2007/0191724 A1* | 8/2007 | Hirsh | A61B 5/029 600/523 |
| 2015/0205930 A1* | 7/2015 | Shaanan | G06F 19/3418 705/2 |

FOREIGN PATENT DOCUMENTS

| CN | 1689509 A | 11/2005 |
| CN | 101169406 A | 4/2008 |

(Continued)

*Primary Examiner* — Namitha Pillai
(74) *Attorney, Agent, or Firm* — Kory D. Christensen

(57) ABSTRACT

A monitoring device includes: a signal collection unit for collecting physiological parameters for representing a physiological status of a human body; a storage unit for storing guidance information of the physiological parameters, the guidance information corresponding to at least one measurement operation step of the physiological parameters; a processing unit for generating a monitoring interface for the physiological parameters and a measurement operation interface corresponding to current measurement operation step and for associating the guidance information corresponding to the current measurement operation step with the measurement operation interface; and a display unit for displaying at least one of the monitoring interface compris- (Continued)

ing the physiological parameters, the measurement operation interface, and the guidance information.

17 Claims, 4 Drawing Sheets

(51) Int. Cl.
| | |
|---|---|
| *A61B 5/0205* | (2006.01) |
| *G16H 50/30* | (2018.01) |
| *G16H 80/00* | (2018.01) |
| *G16H 40/63* | (2018.01) |
| *G06F 3/0482* | (2013.01) |
| *G08B 21/02* | (2006.01) |
| *A61B 5/029* | (2006.01) |
| *A61B 5/0402* | (2006.01) |
| *A61B 5/024* | (2006.01) |
| *A61B 5/02* | (2006.01) |
| *A61B 5/021* | (2006.01) |

(52) U.S. Cl.
CPC .......... *A61B 5/7475* (2013.01); *G06F 3/0482* (2013.01); *G06F 3/04817* (2013.01); *G08B 21/02* (2013.01); *G16H 40/63* (2018.01); *G16H 50/30* (2018.01); *G16H 80/00* (2018.01); *A61B 5/021* (2013.01); *A61B 5/024* (2013.01); *A61B 5/02007* (2013.01); *A61B 5/029* (2013.01); *A61B 5/02028* (2013.01); *A61B 5/0402* (2013.01); *A61B 5/684* (2013.01); *A61B 5/744* (2013.01); *A61B 5/746* (2013.01); *A61B 2560/0223* (2013.01)

(56) References Cited

FOREIGN PATENT DOCUMENTS

| | | | |
|---|---|---|---|
| CN | 101854973 A | 10/2010 | |
| CN | 102940486 A | 2/2013 | |
| CN | 103027672 A | 4/2013 | |
| CN | 103239295 A | 8/2013 | |
| CN | 104116502 A | 10/2014 | |
| EP | 1716807 A1 * | 11/2006 | ......... A61B 5/14553 |

* cited by examiner

MONITORING DEVICE AND METHOD FOR PROVIDING GUIDANCE INFORMATION DURING A MEASUREMENT OPERATION

CROSS-REFERENCE TO RELATED APPLICATIONS

This application is a continuation of PCT Application No. PCT/CN2015/092133, filed Oct. 16, 2015, for MONITORING DEVICE AND METHOD FOR DISPLAYING MONITORING INFORMATION, which is incorporated herein by reference.

TECHNICAL FIELD

The present disclosure relates to the field of medical monitoring, and in particular to a monitoring device, as well as a method for displaying monitoring information.

BACKGROUND

Patient monitoring systems are commonly used in hospitals, especially in intensive care units (ICUs), for monitoring physiological conditions of patients. A common patient monitoring system includes a bedside monitoring device having one or more sensors attached to the patient to monitor parameter data such as, for example, electrocardiogram (ECG), blood pressure, blood oxygen, blood glucose, temperature, etc.

One important task for medical personnel is to connect various measurement components, such sensors, probes, catheters, etc., to the body of the patient, so as to connect the patient with the monitoring device in order to facilitate data collection and the processing and displaying of data. Generally, different measurement components may have significant differences in structure, appearance, method of operation, matters needing attention, etc. Some measurement components are relatively simple, such as a pulse blood oxygen probe, which is commonly a finger-clip photoelectric sensor. As long as the medical care personnel correctly clamp the patient's finger with the pulse blood oxygen probe and correctly connects the other end of the probe cable to the monitoring device, the monitoring device may then start monitoring the blood oxygen parameter. The operation of a blood pressure measurement component is also relatively simple, such as non-invasive blood oxygen measurement. The medical care personnel must correctly sleeve a blood pressure cuff onto an arm of the patient, after which the monitoring device starts blood pressure measurement in response to start signal input and system settings. By contrast, an invasive blood pressure measurement relates requires puncturing the patient's skin, and the operation thereof is relatively more complicated, have more matters needing attention by medical personnel. Similarly, an ECG measurement component includes a plurality of lead electrodes. The process of connecting the electrodes needs to ensure the correct electrode placement and involves coating electrode pads with conductive paste, making the operation thereof relatively complicated. Overall, these parameters are common or traditional basic measurement parameters in the field of monitoring, and may be mastered by general medical care personnel after appropriate training.

However, the operation of new parameter techniques is usually too complicated to remember, which discourages use by medical care personnel discouraged and hinders the pace of adoption of these techniques in clinical applications. Although in the initial stage of clinical generalization of new parameter techniques, suppliers of monitoring device may perform specialized trainings for medical care personnel, which trainings requires significant manpower and resources. The effect of training is usually limited because the scope of the training is unable to cover all medical care personnel who may possibly use these parameter techniques. In addition, during training, the lack of hands-on operations and being unable to repeatedly operate and practice make the medical care personnel quickly forget the techniques after a period of time, and they usually cannot clearly remember how to use these parameter techniques when needed.

Moreover, the suppliers may also provide a user manual regarding new parameter technique applications for the medical care personnel. However, such documents usually have engineered wording, complicated contents and non-prominent emphasis. The medical care personnel are unwilling to spend a lot of time to read these "tomes" while operating the apparatus when needed.

Some suppliers may also provide a quick operation card regarding new parameter technique, which focus on application key points for medical care personnel. Such cards are more concise and easily understood than user manuals and may be prominently displayed, such as hanging above the device to be operated.

Unfortunately, the quick operation card also has a number of disadvantages. First, the card is easily damaged or lost, because the quick operation card is generally made of paper and is hung above the apparatus for a long time. Second, the content is limited, because he quick operation card is usually small and may only provide some key operating instructions. As a result, it is unable to provide more in-depth content regarding parameter principles, including the range of applications and matters needing attention from the medical care personnel. In addition, the quick operation card may only provide text and picture instructions, and has a limited guidance effect for some complicated operational steps, which need to be demonstrated dynamically. Third, error detection and error reporting cannot be performed, because the quick operation card may only passively present correct or incorrect operating instructions, but when a user has an incorrect operation, the quick operation card cannot detect the error and report the error, and is unable to remind the user to correct the error in time to be effective. A relatively new measurement parameter may be complicated and not frequently used by the medical care personnel. Even where training has performed, it is difficult for new measurement parameters to be as easy as measuring the blood oxygen parameter, especially where measurement is appropriate only for patients with severe conditions. Such integrated environments currently result in relatively low use friendliness when the monitoring device is used to measure advanced parameters, such as Pulse Contour Cardiac Output (PiCCO), a thermodilution technique that calculates volumetric measurements of preload and cardiac output.

SUMMARY

The present disclosure includes a monitoring device and a method for displaying monitoring information. In one embodiment a monitoring device includes: a signal collection unit for collecting physiological parameters for representing the physiological status of a human body; a storage unit for storing guidance information of the physiological parameters, the guidance information corresponding to at least one measurement operation step of the physiological parameters; a processing unit for generating a monitoring interface for the physiological parameters and a measurement operation interface corresponding to current measurement operation step, and for associating the guidance information corresponding to the current measurement operation step with the measurement operation interface; and a display unit for displaying one or a combination of the monitoring interface includes the physiological parameters, the measurement operation interface, and the guidance information.

In one embodiment, a method for displaying monitoring information includes: collecting physiological parameters for representing the physiological status of a human body; storing guidance information of the physiological parameters, wherein the guidance information corresponds to at least one measurement operation step of the physiological parameters; generating a monitoring interface for the physiological parameters and a measurement operation interface corresponding to current measurement operation step, and associating the guidance information corresponding to the current measurement operation step with the measurement operation interface; and displaying at least one of the monitoring interface including the physiological parameters, the measurement operation interface, and the guidance information.

The above monitoring device or method for displaying monitoring information may increases convenience and correctness of user operations, and improves user friendliness of the monitoring device, enhancing a user's experience.

DETAILED DESCRIPTION

Figure 1:
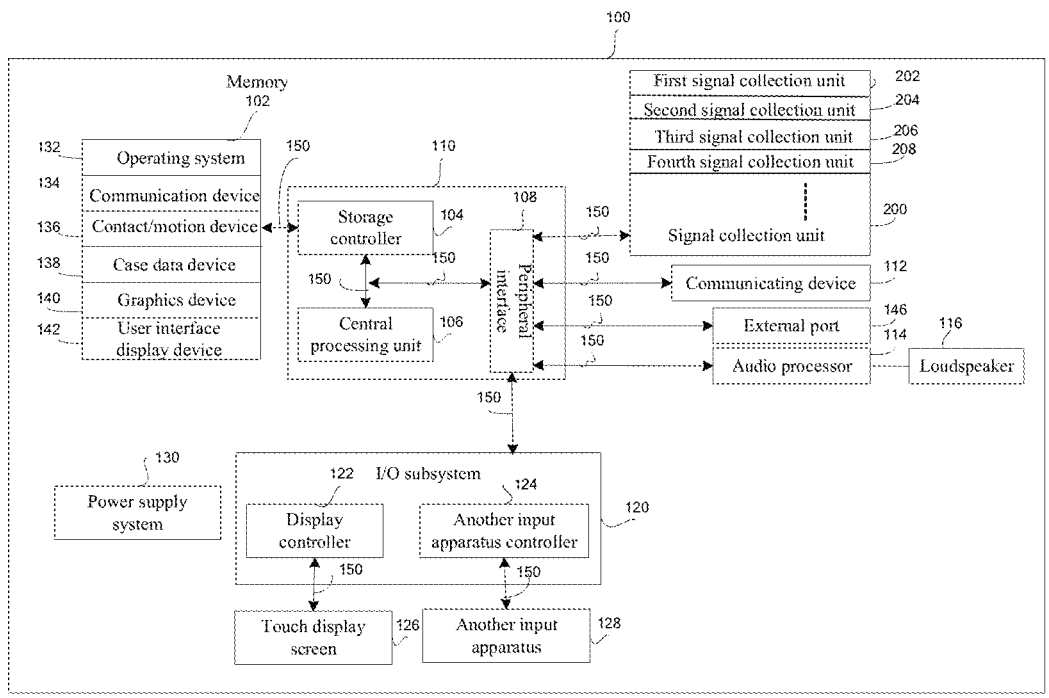
FIG. 1 is a schematic diagram of system composition of a monitoring device.

The present application is further described in detail below with specific embodiments and in conjunction with the accompanying drawings. In the following embodiments, many details are described so that the present application may be better understood. However, it would appreciated by those skilled in the art that some features may be omitted in different cases, or may be substituted by other elements, materials and methods. In certain cases, some operations relevant to the present application are not displayed or described in detail in order to not obscure the inventive aspects. However, for those skilled in the art, describing these relevant operations in detail is not necessary, and they may completely understand relevant operations according to the description and general technical knowledge in the art.

In addition, the characteristics, operations or features described in the description may be combined in any appropriate manner to form various embodiments. Moreover, the steps or actions in the method description may also be exchanged or adjusted in order in a way that would be known to those skilled in the art. Therefore, various orders in the description and accompanying drawings are merely to clearly describe a certain embodiment and do not mean a necessary order, unless specified otherwise.

In various embodiments, the monitoring system has a touch display screen with a graphical user interface (GUI), one or more processors, and a memory including one or more modules, programs or instruction sets for executing multiple functions. These functions may include remote video conferencing, picture/graphic browsing, a pathological database, calendar information, patient file information display, patient directory information display, etc. The modules, programs or instructions for executing the functions may be contained in a computer program product, such as a non-transitory computer readable medium, for execution by one or more processors.

In various embodiments, the monitoring system may be a multi-function monitoring device having a touch screen or touch display screen. A common actual structure (such as the touch display screen) of the above system may support a variety of applications having an intuitive GUI. The above interface control objects may be implemented with computer languages such as Visual Basic (VB) and Java, which may generate graphical objects displayed on the GUI. The graphical objects may include one or a combination of graphics, text, picture, etc.

An application or function utilizing a gesture input of the touch display screen may be used. Alternatively, a hardware input apparatus (e.g., click wheel, keyboard, mouse, and/or joystick) may also be included to execute an operation similar to the above gesture input on the GUI, for example, a cursor is controlled by the hardware input apparatus to move on the GUI to generate an operation action presented on the GUI similar to the gesture input.

An environment in which the various embodiments of the present disclosure may operate is introduced in detail in conjunction with the accompanying drawings. In the following detailed description, many specific details are provided for comprehensive understanding of the embodiments of the present disclosure. However, for those of ordinary skill in the art, it is apparent that the present disclosure may also be implemented without these specific details.

In one embodiment of the present disclosure, FIG. 1 provides some embodiments of a hardware and/or software architecture relevant to the above system.

Referring to FIG. 1, a functional structural block diagram is shown of a medical monitoring system 100 with a touch display screen 126. The monitoring system 100 may include a memory 102 including one or more computer readable storage mediums, a storage controller 104, a central processing unit 106 (which may include one or more processors and/or controllers), a peripheral interface 108, an I/O subsystem 120, a display controller 122, a touch display screen 126, other input apparatus controller 124 and other input apparatus 128. The monitoring system 100 may further include a communication module 112, an audio processor 114, a loudspeaker 116, a signal collection unit 200, an external port 146 and a power supply system 130 (including a DC/DC conversion circuit and/or an AC/DC conversion circuit). The above various elements or modules may intercommunicate on one or more communication buses or signal lines 150.

The memory 102 may include a high-speed random access memory, and may also include a non-volatile memory, such as one or more magnetic disk storage devices, flash memory devices, or other non-volatile solid-state storage devices. In some embodiments, the memory 102 may further include storage remote from the one or more processors 106, such as network attached memory accessed via the communication module 112 or the external port 146 and a communication network (not shown), which may include the Internet, one or more internal networks, a local area network (LAN), a wide area network (WAN) and a storage area network (SAN), etc., or an appropriate combination thereof. The storage controller 104 may control the access to the memory 102 from other assemblies such as the CPU 106, the peripheral interface 108 and the like of the monitoring system 100

The peripheral interface 108 couples input and output peripherals connected to the monitoring system 100 with the central processing unit 106. The central processing unit 106 runs or executes various software programs and/or instruction sets stored in the memory 102 so as to execute various functions and applications of the monitoring system 100 and process data.

In various embodiments of the present disclosure, the peripheral interface 108, the central processing unit (CPU) 106 and the storage controller 104 may be implemented, for example, on a single chip 110. In some embodiments, they may also be implemented on a plurality of separate chips.

The communication module 112 is configured to receive a communication signal, convert the same into an electrical signal and convert the electrical signal into a communication signal to transmit. The communication module 112 may be implemented using known techniques and enables the monitoring system 100 to communicate with an external network or other external apparatus. For example, the communication module 112 can connect to the Internet and Intranet of the World Wide Web (WWW) and/or a wireless and/or wired network such as a cellular telephone network, a local area network (LAN) and/or a metropolitan area network (MAN) to communicate with other systems and devices. The communication module 112 can use any one of a variety of communication standards, protocols and techniques, including but not limited to utilizing a wired or wireless medium, including Bluetooth, Ethernet, 802.11(x), a body area network or other wireless protocols.

The audio processor 114 and the loudspeaker 116 provide an audio interface between users (health personnel) and the monitoring system 100. The audio processor 114 may receive audio data from the peripheral interface 108, convert the audio data into an electrical signal, and send the electrical signal to the loudspeaker 116. The loudspeaker 116 converts the electrical signal into sound waves which may be heard by humans. The peripheral interface 108 may retrieve audio data from the memory 102 and/or the communication module 112 and/or send audio data to the memory 102 and/or the communication module 112.

The I/O subsystem 120 couples the touch display screen 126 and the other input apparatus 128 with the peripheral interface 108. The I/O subsystem 120 may include the display controller 122 and one or more other input controllers 124 to control the other input apparatus 128. The one or more other input controllers 124 receive/send an electrical signal from/to the other input apparatus 128. The other input apparatus 128 may include an actual button and a similar apparatus, a drive plate, a slide switch, a joystick, a click wheel, etc. In some embodiments of the present disclosure, the one or more other input controllers 128 may be coupled with any one or more apparatus of a keyboard, an infrared port, a USB port and a mouse, for example.

The touch display screen 126 provides a gesture input interface between the monitoring system 100 and the user, wherein the gesture input interface is implemented mainly by means of a GUI object of a virtual button, soft keyboard, etc. provided on the GUI of the touch display screen 126. The display controller 122 sends an electrical signal to the touch display screen 126 and/or receives an electrical signal from the touch display screen 126. The touch display screen 126 displays a visualized output to the user. The visualized output may include one or a combination of more of a graphic, text, an icon, a picture, etc., which are collectively referred to as a "graphic" herein.

The touch display screen 126 has at least one touch-sensitive surface to receive a gesture input from the user according to touch and/or contact. The display controller 122 calls a relevant module and/or instruction set in the memory 200 to provide a GUI by displaying graphics on the touch display screen 126, detects a gesture input from the user sensed by the touch-sensitive surface, and converts the detected gesture input into a GUI object (such as one or more soft keys, icons or buttons) displayed on the touch display screen 126, so as to realize interaction between the touch display screen 126 and the user. In one embodiment of the present disclosure, the contact operation position between the touch display screen 126 and the user corresponds to the contact position of a direct contact between an input object, such as a user finger, and the touch display screen 126, or a mapping position of the spatial position when the input object, such as a user finger, approaches the touch display screen 126 mapped onto the touch display screen 126.

The touch display screen 126 may use an LCD (liquid crystal display) technique or LPD (luminescent polymer display) technique, but may also use other display techniques, for example, an OLED display, in other embodiments. The display screen in the touch display screen 126 and the display controller 122 may utilize any one of a variety of touch sensing techniques which are currently known or will be developed in the future to detect the contact in the gesture input and any motion or interruption thereof, these touch sensing technique including but not limited to capacitance, resistance, infrared, surface acoustic wave techniques, image recognition-based or data glove-based gesture input techniques, and a sensor array or other elements for determining the proximity between the input object and one or more contact points on the surface of the touch display screen 126.

The monitoring system 100 further comprises a power supply system 130 for providing a power input for various elements or modules or circuits, which includes a power management system, one or more power sources (such as a battery and alternating current (AC)), a charging system, a power failure detection circuit, a power converter or inverter, a power state indicator (for example, a light emitting diode (LED)), and any other components relevant to the generation, management and distribution of power in the monitoring system 100. According to different power sources, the power supply system may contain a DC/DC conversion circuit, or contain an AC/DC conversion circuit.

The monitoring system 100 may further include a signal collection unit 200, and the signal collection unit 200 detects at least one physiological parameter related to a monitored object and acquires parameter data corresponding to the at least one physiological parameter. The at least one piece of physiological parameter data (biological information) related to the monitored object may be multi-monitoring parameter data (information) related to the electrocardiogram (ECG), non-invasive blood pressure (NIBP), heart rate (HR), oxyhemoglobin saturation (SpO2), end-tidal carbon dioxide concentration (EtCO2), body temperature, cardiac output (CO), pulse rate and anesthetic gas analysis, etc. The signal collection unit 200 includes one or more one or more signal collection units related to the above plurality pieces of physiological parameter data (information). The signal collection unit 200 may be a sensor unit which collects an original physiological parameter signal, and may also be a parameter collection and processing device with a processing or storage function, a common form of the latter being a parameter device of a plug-in type monitoring instrument. According to one classification, a non-invasive measurement parameter is a general parameter, and an invasive or minimally invasive measurement parameter is an advanced parameter; and a certain one or certain type of parameter may also be set as advanced parameters, e.g., hemodynamic parameters are set as advanced parameters, and temperature, pulse rate, ECG, etc. are set as general parameters.

In some embodiments, the memory 102 includes an operating system 132, a communication device (or instruction set) 134, a contact/motion device (instruction set) 136, a case data device (or instruction set) 138, a graphics device (or instruction set) 140 and a user interface display device 142.

The operating system 132 (such as Linux, Unix, OS, Windows or an embedded system like Vxworks) includes various software components and/or drivers which are configured to control and associated conventional system tasks (such as memory association, storage device control, power supply management, etc.) and helpful to communication between various software and hardware.

The communication module 134 is helpful to communicate with other apparatuses via one or more external ports 146, and further comprises various software modules to process data received by the external port(s) 146. The external port 146 (such as a universal serial bus (USB), FireWire, etc.) is appropriate for being directly or indirectly via a network (such as the Internet, a wireless LAN, etc.) coupled with other apparatus.

The contact/motion module 136 and the touch screen display controller 122 together detect the contact with the touch screen 126. The contact/motion module 136 includes various software components to execute various operations associated with contact detection with the touch screen 126, the operations, for example, including determining whether there is a contact, determining whether the contact is moving, and tracking the movement on the touch screen 126 and determining whether the contact is interrupted (i.e. whether the contact is stopped). The operation of determining the movement of a contact point may include determining the rate (amplitude), velocity (amplitude and direction) and/or acceleration (including the amplitude and/or direction) of the contact point.

The graphics module 140 includes various known software components to present and display graphics on the touch screen 126. As used herein, "graphic" may include any object that may be displayed to a user, including but not limited to text, icons (for example, a user interface object including a software key), digital images, waveforms, numerical values, etc.

In some embodiments, the user interface module 142 controls the display of a GUI of the monitoring system 100. When the user interface module 142 detects one or more instructions satisfying any one condition for GUI display, then the corresponding graphical interface is switched to for display. More details related to the GUI will be described hereinafter.

FIG. 1 above only refers to a structural block diagram of a medical monitoring system 100, and the monitoring system 100 is merely an example of a type of medical monitoring equipment. The monitoring system 100 above may also have more or fewer elements or modules than FIG. 1, and may also use two or more elements or modules above in combination, or may also perform arrangement of different configurations on the architecture in FIG. 1. The various elements or modules shown in FIG. 1 may be implemented in the form of hardware, software, or a combination of hardware and software, including one or more signal processing and/or application-specific integrated circuits (ASICs).

The monitoring device described in FIG. 1 may be a multi-parameter monitoring instrument, which may be implemented within a single device, as a plug-in type monitoring instrument, or as a component of a central station monitoring system. Various devices and components described thereby may be correspondingly combined or separated, etc. according to these different implementation formats.

Figure 2:
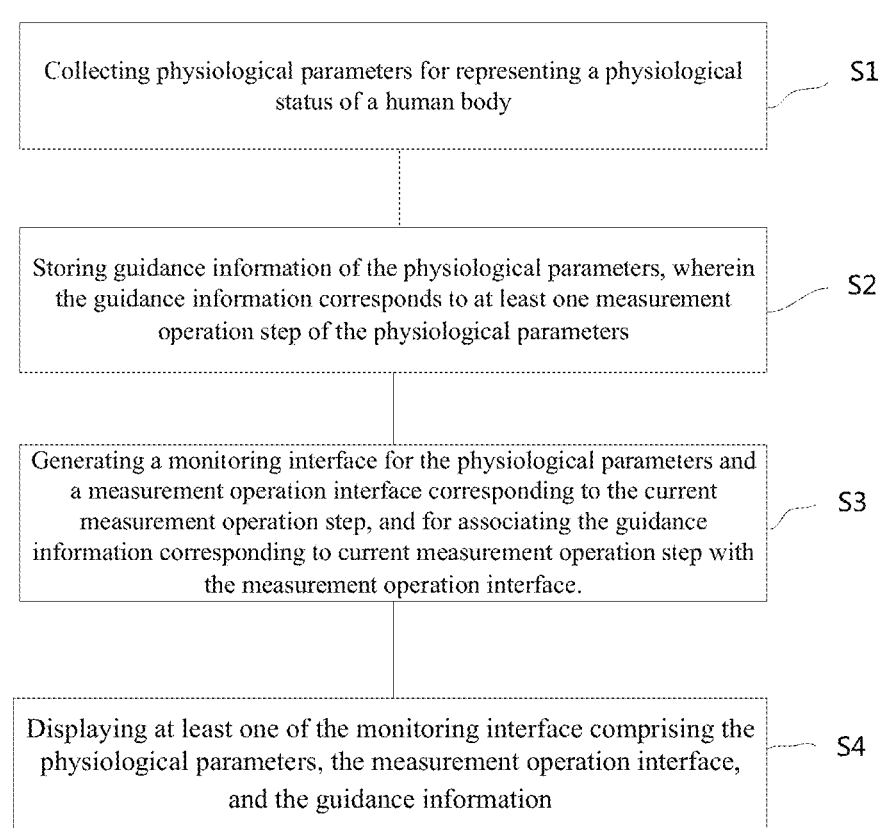
FIG. 2 is a schematic flowchart of a method for displaying monitoring information.

FIG. 2 is a flowchart of a method for displaying monitoring information of one embodiment of the present disclosure. The method may include steps S1-S4.

S1, collecting physiological parameters for representing a physiological status of a human body.

The physiological parameters may be collected via a signal collection unit, so as to obtain the original physiological parameter data or obtain the calculated, analyzed or processed physiological parameters. The physiological parameters may include general parameters and advanced parameters, and may be invasive, minimally invasive, or non-invasive measurement parameters.

S2, storing guidance information of the physiological parameters, wherein the guidance information corresponds to at least one measurement operation step of the physiological parameters.

The guidance information may be stored in a storage unit. In one embodiment, the storage unit stores a lookup table between various measurement operation steps of one physiological parameter with guidance information corresponding thereto. For example, the measurement operations of minimally invasive hemodynamic parameters include a thermodilution measurement step and a setup step, and the lookup table between the guidance information of the thermodilution measurement step with the guidance information of the setup step may be stored. In addition, the lookup table may also be multi-level, for example, the guidance information corresponding to the setup step may further be divided into the guidance information of alarm limit setting, the guidance information of measurement setup, and the guidance information of parameter selection; and an entry may also be individually provided otherwise to centrally store help information corresponding to the physiological parameters.

S3, generating a monitoring interface for the physiological parameters and a measurement operation interface corresponding to current measurement operation step, and associating the guidance information corresponding to the current measurement operation step with the measurement operation interface.

The monitoring interface or measurement operation interface may be generated via a processing unit or a control unit. With regard to different measurement operation interfaces of the same parameter, the corresponding guidance information is read and associated with the measurement operation interface. The method of association includes generating a popup window, information box, etc. containing the guidance information, so as to associate the current measurement operation step with the current guidance information.

S4, displaying at least one of the monitoring interface including the physiological parameters, the measurement operation interface, and the guidance information.

The physiological parameter information, operation information, and/or the guidance information is displayed according to the generated interface, as described in greater detail below.

As noted earlier, the order of steps disclosed above should not be understood as a limit to the scope of the present disclosure. Various orders may be implemented within the scope of the disclosure.

Figure 3:
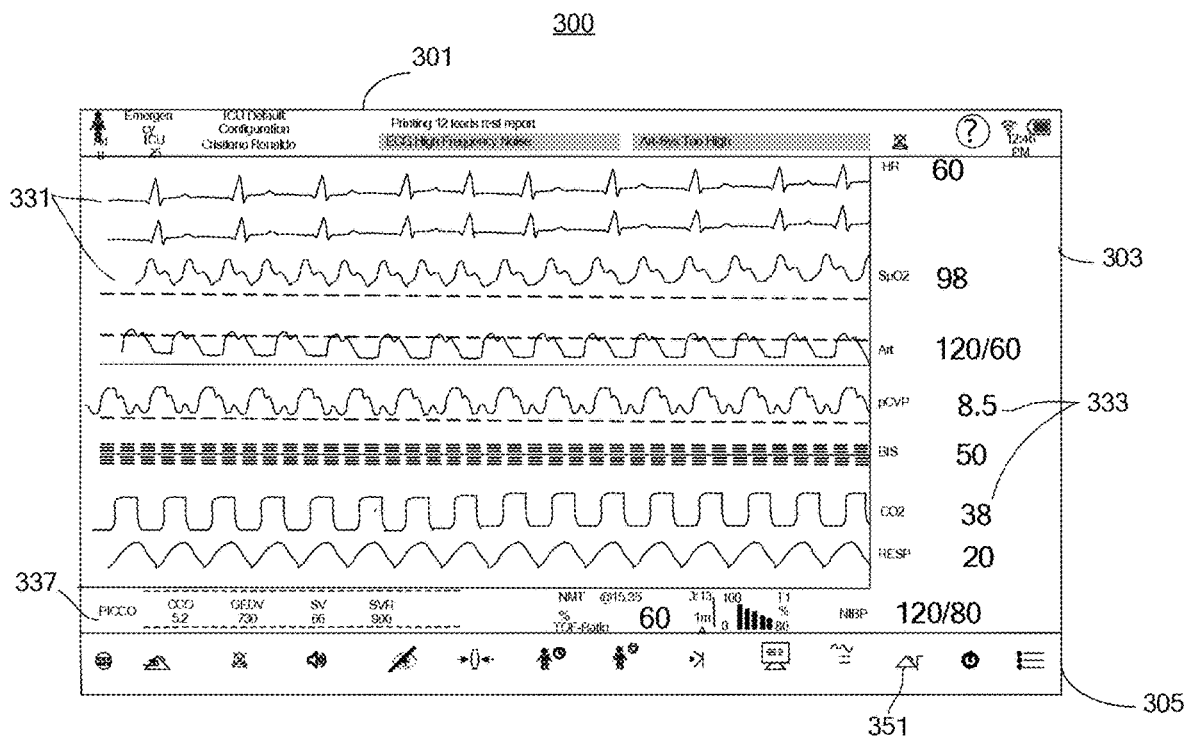
FIG. 3 is a schematic diagram of a monitoring interface corresponding to a method for displaying monitoring information.

FIG. 3 is a first user interface generated by a method for displaying monitoring information. The interface is a main monitoring interface 300, that is, a measurement result display interface or monitoring interface. For the convenience of description, if there is no special illustration, "main interface" will be the abbreviation of the main monitoring interface hereinafter. The main interface 300 includes display of various current monitoring information, including but not limited to parameter waveforms, numerical parameter information, etc., at the current moment. In order to facilitate a medical care personnel to view some basic information relevant to a patient, or call out or adjust the contents displayed on the main interface 300 according to requirements, a title area 301 and a menu configuration area 305 are respectively provided at the top and bottom of the main interface 300, so as to perform some required operations. Between the title area 301 and the menu configuration area 305 is a waveform data display area 303. The title area 301 may display a patient name, a gender, bed information, electric quantity status of the monitoring device, network signal status of the monitoring device, current time, etc. The menu configuration area 305 may be used for providing status icons of alarm mute, display configuration, alarm configuration, review, standby, etc., and a corresponding function may be set by clicking a certain corresponding icon, for example, clicking an alarm configuration icon 351 may set an alarm mode, an alarm level for an event, etc.

Figure 4:
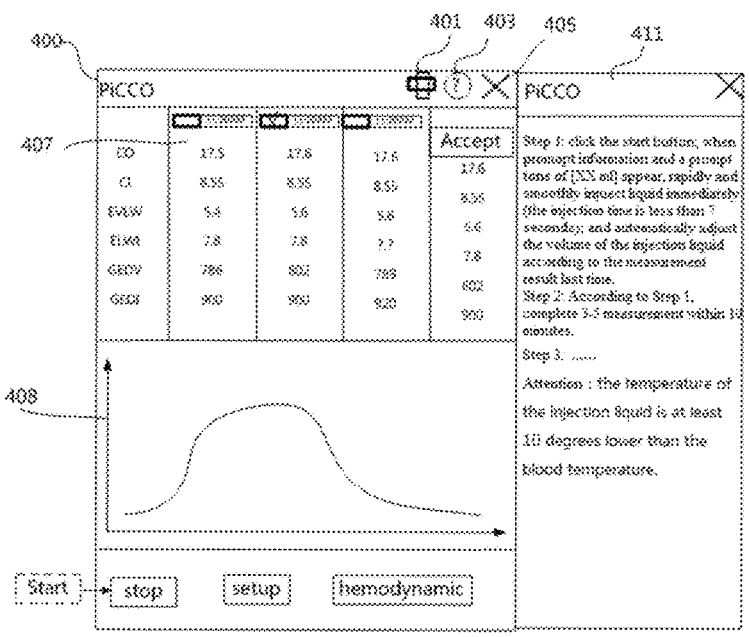
FIG. 4 is a schematic diagram of a measurement interface corresponding to a method for displaying monitoring information.

The waveform data display area 303 displays monitoring information about the patient. In this embodiment, displaying real-time monitoring information is taken as an example. In some other embodiments, the waveform data display area 303 may be replaced with historical monitoring information about the patient, and the real-time monitoring information and the historical monitoring information may also be displayed at the same time. The specific interface arrangement is not described in detail herein. The waveform data display area 303 may be further divided into display areas or regions. As shown in FIG. 4, the waveform data display area 303 may display waveforms 331 of multiple parameters at the left side, and display multiple numerical parameters 333 at the right side. For most parameters or measurement components, information about the parameter may be represented by one or two waveforms and/or one or two parameter numerical values, for example, with regard to the blood pressure parameter, blood pressure information about the patient may be seen from the blood pressure parameter value. However, with regard to relatively novel or complicated measurement such as PiCCO, since traditional multi-parameter monitoring instruments seldom integrate such parameters, they are referred to as advanced parameters herein.

PiCCO, which is minimally invasive, is mainly used for measuring hemodynamic parameters of patients with severe conditions and utilizes a pulmonary thermodilution technique and a pulse waveform contour analysis technique to measure a single cardiac output (CO), and obtains a continuous pulse contour cardiac output (PCCO) by analyzing the area under the arterial pressure waveform curve, and at the same time may calculate a variety of hemodynamic parameters such as the intrathoracic blood volume (ITBV) and extravascular lung water (EVLW), pulse contour cardiac output index (PCCI), arterial pressure (AP), heart rate (HR), stroke volume (SV), stroke volume index (SVI), stroke volume variation (SVV), systemic vascular resistance (SVR) and systemic vascular resistance index (SVRI). The measurement component of PiCCO includes an arterial catheter, and the arterial pressure may be measured via the arterial catheter; in addition, the measurement component further includes a deep venous catheter for injecting ice brine, only then the arterial catheter may obtain a temperature response curve to calculate various relevant parameters, and the cardiac output needs to be measured for three times at the beginning stage for correction. Moreover, since the measurement may obtain a variety of parameters and the various parameters have different clinical significances and generally may not be all displayed at the same time, usually a medical care personnel needs to make a selection.

As shown in FIG. 4, the waveform data display area 303 contains an advanced parameter display area 337. In the advanced parameter display area 337, hemodynamic parameters obtained through PiCCO measurement are displayed, such as CCO and GEDV. Since there may be a plurality of hemodynamic parameters obtained through PiCCO measurement, the hemodynamic parameters that may be set up by a user are to be displayed in the advanced parameter display area 337, as described below. The main interface 300 may further include a help label (a symbol of a circle with a question mark in the figure). Starting the label may enter a help system of the monitoring device to view help information about measurement of different physiological parameters.

FIG. 4 is a second user interface, i.e. a thermodilution measurement interface, generated by a method for displaying monitoring information. In one embodiment, the advanced parameter display area 337 of the main interface 303 is operated, such as clicking, touching and controlling, and then an advanced parameter measurement interface 400 may be entered. The advanced parameter measurement interface may be a floating window floating above the main interface 300. The advanced parameter measurement interface 400 includes some functional icons, such as a print icon 401, a guidance icon 403 and a close icon 405 provided at the upper right corner or other suitable location. Clicking the print icon 401 may print information such as the current measurement result, etc., and clicking the close icon 405 may close the current advanced parameter measurement interface 400, so as to return the main interface 300. The main function of the measurement interface is to provide some operation entries required for the user to perform measurement. A plurality of command buttons are provided at the bottom of the advanced parameter measurement interface 400, including Stop, Setup and Hemodynamic, representing stop, setup and hemodynamic respectively. The stop button may also be a Start button at the same time, and clicking the Start button before measurement may enter a measurement process, i.e. starting the thermodilution measurement. When a prompt and a prompt tone of xx ml (injection volume of ice brine) appear on the interface, the medical care personnel need to follow the prompted injection volume for a smooth and rapid injection. After the injection, the monitoring device completes measurement automatically and outputs a group of measurement values, such as CO, CI and EVLW, and a thermodilution waveform.

The advanced parameter measurement interface 400 further includes a calibration selection area 407 and a thermodilution waveform area 408. The measurement values obtained in the above step are displayed in the calibration selection area 407, and the thermodilution waveform of this measurement is displayed in the thermodilution waveform area 408. After performing thermodilution measurements three times, three groups of data are correspondingly obtained. In one embodiment, the average value of the three groups of data is taken automatically as a calibration value. In another embodiment, a user selection box may be provided, clicking and checking one of the three groups of data as a calibration value. The Accept button in the interface is taken as a confirm key of calibration selection. In still another embodiment, thermodilution measurements may be performed three or more times, so as to obtain three or more, such as five, measurement values. The user may select three of the five groups of measurement values and click the confirm key (Accept), and the monitoring system calculates an average value of the selected three groups of measurement value as the calibration value.

The method for displaying monitoring information provided by the present disclosure further provides sectional guidance or help. Specifically, when it comes to the thermodilution measurement stage, if the medical care personnel are in doubt or uncertain about the measurement, the guidance icon 403 may be clicked, and then a prompt information window 411 of the measurement stage may be called out. The prompt information window 411 includes operation steps or some important steps required for measurement, and may also prompt with matters that need attention. When the prompt information window 411 of the measurement stage is no longer required, it may be closed. In one embodiment, the prompt information window 411 and the advanced parameter measurement interface 400 are arranged in parallel, and are not overlapping with each other.

Figure 5:
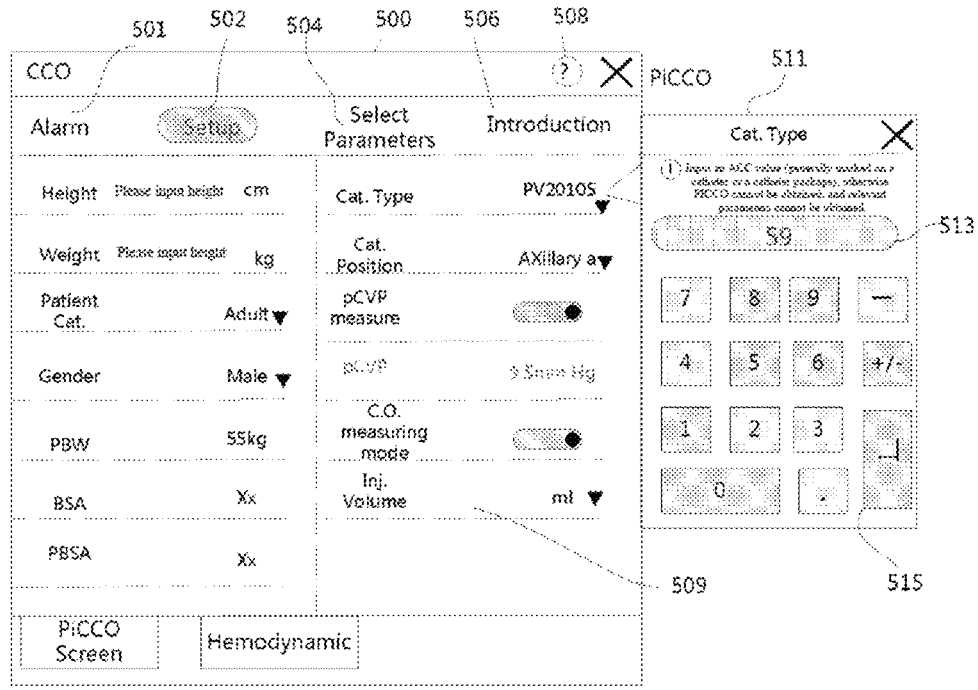
FIG. 5 is a schematic diagram of a setup interface corresponding to a method for displaying monitoring information, which displays the contents of one setup subinterface.

Clicking the Setup button enters a setup interface. Referring to FIG. 5, there is shown a third user interface, i.e. a setup interface 500, generated by a method for displaying monitoring information of one embodiment of the present disclosure. The setup interface 500 includes a plurality of menu labels, such as an alarm label 501, a setup label 502, a parameter selection label 504 and an introduction label 506. These menu labels are provided in an area near the top of the setup interface. When a user clicks one label thereof, a corresponding subinterface is entered. For example, clicking the setup label 502 enters a measurement setup subinterface 509, displaying contents relevant to setup. When a certain option that needs to be set up is clicked, such as a height (Height) option, a height numerical value may be input in the blank zone of the option. In some embodiments, prompt information such as "please input height" may be prompted in the blank zone. Some other function switch type options provide corresponding selection switches. The setup interface 500 provides a great variety of option setup forms to facilitate user operations. In some other embodiments, the option may have a pull-down numerical value selection function. The setup interface 500 further provides sectional guidance or help. Specifically, when a certain option is set up, clicking a guidance label 508 may call out a setup prompt window 511. Certainly, the setup prompt window 511 may also be popped up automatically when the user clicks the option. For example, when the user clicks and selects a catheter type option (Cat. Type), the setup prompt window 511 is popped up at the right side of the setup interface 500. The setup prompt window 511 and the setup interface 500 are arranged in parallel, and are not overlapped with each other. The area of the setup prompt window 511 is less than that of the setup interface 500, and may have a close label. The setup prompt window 511 includes prompt information, an input field 513 and a soft keyboard 515. The prompt information and an operation entry relevant to the setup of one option are integrated into the setup prompt window 511. The setup of the option may be accomplished by only needing to input a numerical value in a setup prompt box of the corresponding option, without returning to the setup subinterface 509 to perform a setup operation, and in this way, a medical care personnel may accomplish operations conveniently with the help of the guidance.

Figure 6:
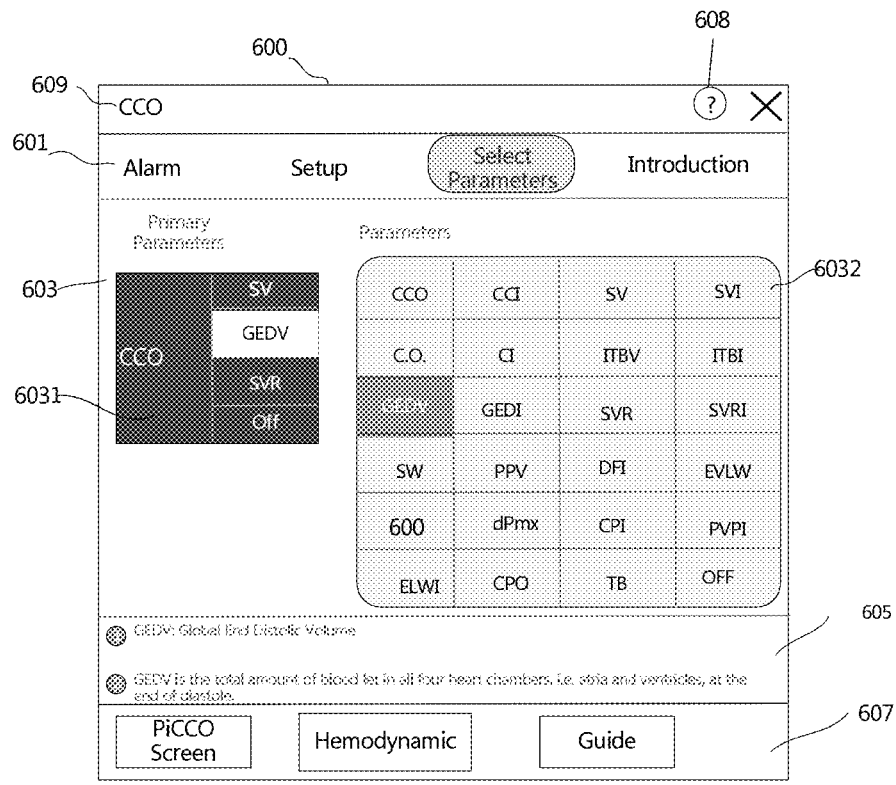
FIG. 6 is a schematic diagram of a setup interface corresponding to a method for displaying monitoring information, which displays the contents of one parameter selection subinterface.
Figure 7:
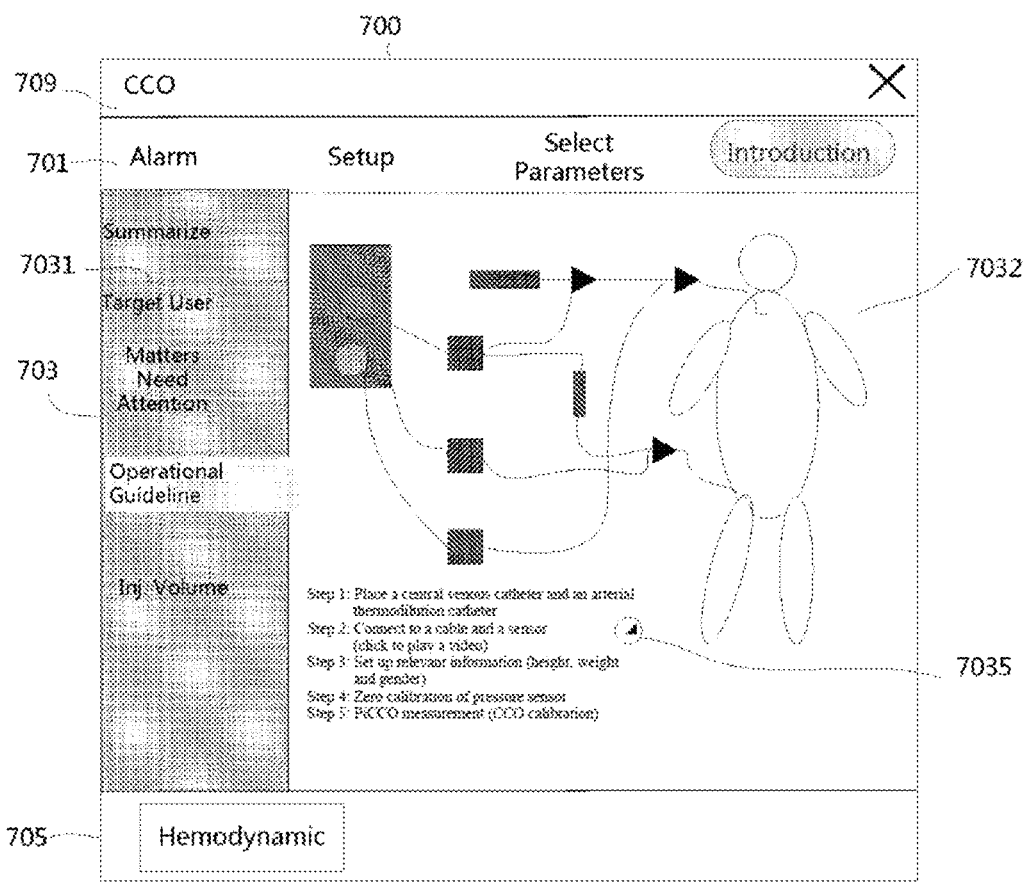
FIG. 7 is a schematic diagram of a setup interface corresponding to a method for displaying monitoring information, which displays the contents of one introduction subinterface.

FIG. 6 is a fourth user interface, i.e. a parameter selection subinterface 600, generated by a method for displaying monitoring information of one embodiment of the present disclosure. The parameter selection label 504 of the setup interface 500 is selected, after which the interface switches to the parameter selection subinterface 600. The parameter selection subinterface 600 includes a menu label area 601, a parameter selection area 603, a guidance area 605 and a command button area 607 which are sequentially arranged from top to bottom, and may further include a title area 609 provided above the menu label area 601. The direction from top to bottom may also be described as a perpendicular or vertical direction, and similarly, the direction from left to right may be described as a horizontal or transverse arrangement. The menu label area 601 is basically the same as the menu label area in the setup interface 500, and will not be described again herein. The parameter selection area 603 includes two subareas which are arranged in parallel at left and right but with different area sizes: a selected area 6031 and an area to-be-selected 6032. According to the presetting of the monitoring system, the number of parameters displayed in the selected area 6031 is less than the number of parameters displayed in the area to-be-selected 6032, wherein the selected area 6032 may include all the parameters that may be calculated according to the thermodilution measurement, i.e. a set or a subset of minimally invasive hemodynamic parameters, while the area to-be-selected 6031 correspondingly displays the parameters according to the user's selection, and the parameters of the selected area 6031 may finally be displayed in the advanced parameter display area 337 of the main interface. The parameters of the selected area 6031 may all be changed correspondingly according to the selection of the user from the area to-be-selected 6032, wherein some parameters may also be selected all the time by default by the monitoring system, for example, CCO is selected by default, while parameters such as SV and GEDV need to be selected by the user himself/ herself from the area to-be-selected 6032. In some embodiments, the number of parameters in the selected area 6031 is fixed, and in some embodiments, an extension label may also be provided so that the user may increase the number of parameters in the selected area, that is, the user may set the number of parameters displayed in the advanced parameter display area 337. The user may select the same number of parameters as preset parameters in the selected area 6031, and may also select fewer parameters than the preset parameters. In addition to the parameters, the area to-be-selected 6032 may further provide a blank or OFF option.

The guidance area 605 is used for displaying detailed information or explanation relevant to the parameters of the area to-be-selected 6032 or the selected area 6031. In one embodiment, in the area to-be-selected 6032, a certain parameter is selected currently, for example, the parameter is GEDV, after which, at this moment, the guidance area 605 displays guidance information corresponding to the currently selected parameter. The guidance area 605 may be opened or closed by the guidance label 608 provided in the title area 609.

Please refer to FIG. 8, which is a fifth user interface, i.e. an introduction subinterface 700, generated by a method for displaying monitoring information of one embodiment of the present disclosure. The introduction label 506 of the setup interface 500 is selected, after which the interface switches to the introduction subinterface. The introduction subinterface 700 is an overall guidance interface, which is not directly associated with the operation steps of the measurement, setup, etc., of advanced parameters, but an entry to help information corresponding to the advanced parameters which is stored in the monitoring system in advance, for a user to systematically view or learn all help information relevant to the advanced parameters. Being different from the traditional monitoring instruments, this embodiment provides guidance information corresponding to an advanced parameter by an introduction interface embedded in an advanced parameter setup interface, rather than providing a unified entry to help information related to all monitoring parameters on the main interface, and the viewing for guidance information is more targeted. The introduction subinterface 700 may include a title area 709, a menu label area 701, a guidance information area 703 and a functional button area 705 which are sequentially arranged vertically. The guidance information area 703 includes a category label area 7031 and a guidance content area 7032 arranged transversely, wherein the category label area 7031 includes five category labels of Summarize, Target Users, Matters Need Attention, Operational Guideline and Inj. Volume, so as to store and present guidance and help information in categories. Clicking a corresponding label may view corresponding guidance or help contents. For example, clicking and selecting the operational guideline category label, the guidance content area 7032 displays a schematic diagram of overall use of an advanced parameter, including placement positions of a sensor and a catheter, and simple textual description may also be added. In some embodiments, the guidance information area 703 further includes a link button 7035, and clicking the button may view animation or a video relevant to the advanced parameter, so as to provide more intuitive help and guidance. Certainly, in some embodiments, the guidance content area 7032 may also directly store help and guidance information in the form of video or animation, motion graph, etc.

In some embodiments, the introduction label and introduction interface may also be omitted, only retaining immediate reminding functions regarding measurement and setup operations.

In some embodiments, if the guidance information under the current menu label is not disabled manually, the current guidance information is closed after the user clicks other menu labels; and the guidance icon may only be valid for the current menu label, and may also be valid for the entire setup interface.

The monitoring device and method for displaying monitoring information provided by various implementations (embodiments) of the present disclosure set sectional operation guidance and help with regard to the advanced parameters, and may call out guidance or help as required by a user, so that the operation correctness of the user may be improved, without interfering the operation flow too much, and operational convenience may be satisfied for different quantity levels of users, thereby improving overall user friendliness. The medical monitoring system, method for displaying monitoring data, and monitoring display device in some embodiments of the present disclosure enhances convenience for a user (medical care personnel) to view parameter data of a patient in the historical monitoring periods, thereby greatly improving the user experience.

The storage herein includes forms of storage and temporary storage, etc. The guidance information involved herein may be displayed on a screen integrated with the monitoring device itself, and may also be displayed on a separate slave screen connected to the monitoring device; and in some embodiments, the guidance information may also be separated from the main interface, measurement interface, setup interface, etc., and is displayed respectively on a main screen and a slave screen of the monitoring device. In some embodiments, when the operation of a user has an error or an anomaly is detected, the guidance information makes a response and reports the error in time, and an entry and prompt, etc. for performing the operations again or checking may also be provided.

The above-mentioned examples merely represent several embodiments, giving specifics and details thereof, but should not be understood as limiting the scope of the present disclosure thereby. It should be noted that a person of ordinary skill in the art may also make several alterations and improvements without departing from the spirit of the present disclosure and these would all fall within the scope of protection of the present disclosure. Therefore, the scope of protection of the present patent of disclosure shall be in accordance with the appended claims.

What is claimed is:

1. A monitoring device, comprising:
   a signal collection unit for collecting physiological parameters for representing a physiological status of a human body;
   a storage unit for storing guidance information corresponding to at least one measurement operation pertaining to the physiological parameters, wherein the guidance information includes a list of a plurality of steps to be carried out by a user during the measurement operation, and wherein the measurement operation comprises at least one of a measurement step, a calibration step and a setup step;
   a processing unit for generating a monitoring interface for the physiological parameters and a measurement operation interface corresponding to a current measurement operation, and for associating the guidance information corresponding to the current measurement operation with the measurement operation interface; and
   a display unit for displaying at least one monitoring interface comprising the physiological parameters, the measurement operation interface, and the guidance information; wherein the measurement operation interface comprises a setup interface and an introduction subinterface embedded in the setup interface, and the guidance information is sectional and is provided by the introduction subinterface;

wherein the physiological parameters comprise minimally invasive hemodynamic measurement parameters, the measurement operation comprises a thermodilution measurement step and a setup step, and the measurement operation interface comprises a thermodilution measurement interface;

wherein the thermodilution measurement interface comprises at least one of a calibration selection area, guidance icon, and a close icon selection; the calibration selection area is used for displaying thermodilution measurement results at least three times and determining a calibration value from a user's selection; the guidance icon is used for the user to open the guidance information corresponding to the thermodilution measurement step; and the close icon is used for closing the guidance information corresponding to the thermodilution measurement step.

2. The monitoring device of claim 1, wherein the setup interface comprises a plurality of menu labels, the menu labels are used for switching among different setup subinterfaces, and the guidance information corresponding to the setup step comprises guidance information corresponding to the different setup subinterfaces.

3. The monitoring device of claim 2, wherein the setup subinterface comprises a setup prompt window; wherein the guidance information corresponding to the setup subinterface is popped up in response to an input operation on the setup prompt window by a user; or the guidance information corresponding to the setup subinterface is displayed in the form of an information box at a side of the setup subinterface, and the information box comprises a prompt corresponding to the setup prompt window and an input field for a user to input information.

4. The monitoring device of claim 3, wherein the setup prompt window allows a user to set up a corresponding option by only receiving a numerical value without returning to the setup subinterface to perform a setup operation.

5. The monitoring device of claim 2, wherein the setup step comprises at least one of a measurement setup subinterface, an alarm setup subinterface and a parameter selection subinterface.

6. The monitoring device of claim 5, wherein the guidance information corresponding to the parameter selection subinterface is embedded in the parameter selection subinterface, the parameter selection subinterface comprises a selected area and an area to-be-selected, and the area to-be-selected collectively displays a set of the minimally invasive hemodynamic parameters.

7. The monitoring device of claim 1, wherein the guidance information is displayed in a prompt information window that is arranged parallel with the measurement operation interface, and wherein the prompt information window and the measurement operation interface do not overlap.

8. The monitoring device of claim 1, wherein the guidance information is displayed in a prompt information window that is arranged parallel with the setup interface, and the prompt information window and the setup interface do not overlap.

9. The monitoring device of claim 1, wherein the setup interface comprises an introduction label for the physiological parameters, which is used for collectively displaying information relevant to the physiological parameters; and the introduction subinterface corresponding to the introduction label comprises a video link button or a plurality of category labels corresponding to different information.

10. A method for displaying monitoring information, comprising:

collecting physiological parameters for representing a physiological status of a human body;

storing guidance information corresponding to at least one measurement operation of the physiological parameters, wherein the guidance information includes a list of a plurality of steps to be carried out by a user during the measurement operation, and;

generating a monitoring interface for the physiological parameters and a measurement operation interface corresponding to current measurement operation, and associating the guidance information corresponding to the current measurement operation with the measurement operation interface; and displaying at least one monitoring interface comprising the physiological parameters, the measurement operation interface, and the guidance information; wherein the measurement operation interface comprises a setup interface and an introduction subinterface embedded in the setup interface, and the guidance information is sectional and is provided by the introduction subinterface;

wherein the physiological parameters comprise minimally invasive hemodynamic measurement parameters, the measurement operation comprises a thermodilution measurement step and a setup step, and the measurement operation interface comprises a thermodilution measurement interface;

wherein the thermodilution measurement interface comprises at least one of a calibration selection area, a guidance icon, and a close icon; the calibration selection area is used for displaying thermodilution measurement results at least three times and determining a calibration value from a user's selection; the guidance icon is used for the user to open the guidance information corresponding to the thermodilution measurement step; and the close icon is used for closing the guidance information corresponding to the thermodilution measurement step.

11. The method for displaying monitoring information of claim 10, wherein displaying at least one of the monitoring interface comprising the physiological parameters, the measurement operation interface and the guidance information comprises: displaying the guidance information corresponding to the thermodilution measurement step in the form of a popup window, and arranging the popup window side by side with the thermodilution measurement interface.

12. The method for displaying monitoring information of claim 10, wherein the setup interface comprises a plurality of menu labels, the menu labels are used for switching among different setup subinterfaces, and the guidance information corresponding to the setup step comprises guidance information corresponding to the different setup subinterfaces.

13. The method for displaying monitoring information of claim 12, wherein the setup step comprises at least one of a measurement setup subinterface, an alarm setup subinterface and a parameter selection subinterface.

14. The method for displaying monitoring information of claim 13, wherein displaying at least one of the monitoring interface comprising the physiological parameters, the measurement operation interface and the guidance information, comprises one of the following steps: popping up the guidance information corresponding to the setup subinterface in response to an input operation on the setup prompt window by a user; and displaying the guidance information corresponding to the setup subinterface in the form of an information box at a side of the setup subinterface, and the information box comprises a prompt corresponding to the setup prompt window and an input field for the user to input information.

15. The method for displaying monitoring information of claim 13, further comprising: embedding the guidance information corresponding to the parameter selection subinterface in the parameter selection subinterface; or
   displaying a set of the minimally invasive hemodynamic parameters in an area to-be-selected, wherein the parameter selection subinterface comprises a selected area and the area to-be-selected.

16. The method for displaying monitoring information of claim 10, wherein the measurement operation comprises at least one of a measurement step, a calibration step and a setup step.

17. The method for displaying monitoring information of claim 10, wherein the setup interface comprises an introduction label for the physiological parameters, which is used for collectively displaying information relevant to the physiological parameters; and the introduction subinterface corresponding to the introduction label comprises a video link button or a plurality of category labels corresponding to different information.

* * * * *